United States Patent [19]

Venturello et al.

[11] Patent Number: 4,532,079

[45] Date of Patent: Jul. 30, 1985

[54] PROCESS FOR THE PREPARATION OF CARBOXYLIC ACIDS STARTING FROM OLEFINES OR VICINAL DIHYDROXY COMPOUNDS

[75] Inventors: Carlo Venturello; Marco Ricci, both of Novara, Italy

[73] Assignee: Montedison S.p.A., Milan, Italy

[21] Appl. No.: 599,678

[22] Filed: Apr. 12, 1984

[30] Foreign Application Priority Data

Apr. 15, 1983 [IT] Italy ............................. 20604 A/83

[51] Int. Cl.$^3$ .................... C07C 51/285; C07C 51/245
[52] U.S. Cl. .................... 260/413; 502/154; 502/155; 502/164; 562/493; 562/538; 562/540; 562/543; 562/544
[58] Field of Search .................... 502/154, 155, 164; 562/493, 538, 544, 540, 543; 260/413 J, 413 HC, 413 M, 413 R

[56] References Cited

U.S. PATENT DOCUMENTS 2,437,648 3/1948 Milos ............................. 260/413 HC

OTHER PUBLICATIONS

J. Am. Oil Chemists Soc. 44 316-320 (1967) Luoug, et al., "Direct Hydroxylation of Fats".
J. Catalysis 19 256-263 (1970) Allan, et al., "Macromolecular Organometallic Catalysis".

Primary Examiner—Natalie Trousof
Assistant Examiner—John T. Sullivan
Attorney, Agent, or Firm—Stevens, Davis, Miller & Mosher

[57] ABSTRACT

Process for the preparation of a monocarboxylic or dicarboxylic acid by oxidative scission of an olefine or its corresponding vicinal dihydroxy compound.

An olefine of the formula $R_1—CH=CH—R_2$ or $R_1—CH=CH_2$ or a vicinal dihydroxy compound of formula $R_1—CHOH—CHOH—R_2$ or $R_1—CHOH—CH_2OH$ (wherein $R_1$ and $R_2$ are either equal to or different from each other, and possibly substituted with groups inert under the reaction conditions, represent hydrocarbon groups such as the alkyls having up to 30 carbon atoms; the cycloalkyls, possibly branched or substituted and having from 3 to 12 carbon atoms; the aryls and alkylaryls having from 6 to 12 carbon atoms; moreover, $R_1$ and $R_2$ may be bound to each other so as to form a cyclic alkenyl or cycloalkyl having up to 12 carbon atoms) are reacted, with vigorous stirring, with $H_2O_2$, at a temperature between 0° and 120° C., and under a pressure of between 1 and 100 atmospheres; and including an aqueous phase containing $H_2O_2$ and an organic phase consisting or consisting essentially of a solvent, the olefine or the vicinal dihydroxy compound, and a catalyst.

8 Claims, No Drawings

PROCESS FOR THE PREPARATION OF CARBOXYLIC ACIDS STARTING FROM OLEFINES OR VICINAL DIHYDROXY COMPOUNDS

DESCRIPTION OF THE INVENTION

The present invention relates to a process for the preparation of carboxylic acids starting from olefines or from their corresponding vicinal dihydroxy compounds.

More particularly, this invention relates to a process according to which carboxylic acids are prepared by the oxidative scission of olefines or of their corresponding vicinal dihydroxy compounds by means of $H_2O_2$, in a biphasic aqueous liquid/organic liquid system, in the presence of suitable catalysts.

Various processes are known for the preparation of carboxylic acids. Among the various different procedures followed, the oxidative scission of olefinic hydrocarbons represents, thanks to the wide availability of the raw material, a particularly attractive way. Olefinic hydrocarbons may be oxidized to carboxylic acids by the use of various oxidizers, such as $KMnO_4$, $K_2Cr_2O_7$ and $RuO_4$. These processes are, however, of little practical interest because of the high cost of the oxidizers used as well as their toxicity (particularly with regard to $RuO_4$) and the serious problems involved in their disposal or their recovery at the end of the reaction.

In the case of ruthenium, in order to obviate in part some of the above drawbacks, there have been suggested quite a number of oxidation processes for the conversion of olefines to carboxylic acids based on the use of a ruthenium compound (for instance $RuCl_3$) in catalytic quantities, combined with the use of various oxidizers such as $NaOCl$, $NaIO_4$, $Ce^{IV}$ salts, $CrO_3$, together with $HNO_3$ and, lastly, organic peracids (for instance, peracetic acid) capable of reoxidizing the reduced catalyst to the maximum valency.

However, in the case of these catalytic procedures, there are encountered in a more or less accentuated way difficulties of an economic and/or environmental character in their practical use. For example, in the case of the use of $NaIO_4$, $NaClO_4$ or $Ce^{IV}$ salts as primary oxidizers, in order to make the process technically feasible it becomes necessary to ensure their complete recovery, an operation that in practice is very difficult.

To these difficulties there must be added problems connected with the purification of the effluent waters from the process. Likewise, in the case of the use of organic peracids, even if there is no problem of polluting effluent waters, there still exist the problems of cost, of recovery, or of use of the acid coming from the peracid.

On the other hand, the catalytic oxidation of olefines to carboxylic acids, using aqueous $H_2O_2$ as a primary oxidizer, offers undoubted advantages with respect to the above-cited methods, thanks to the relatively modest cost of the oxidizer and to the absence of a reduction product to be disposed of. However, this approach has not been the object of any particular interest because of the poor efficiency of $H_2O_2$ as an oxidizer in the above reaction. The few examples reported in the patent literature concern only the oxidation of particularly reactive olefines (that is, cycloolefines) to carboxylic acids; they give rather unsatisfactory yields of acids and are, at any rate, always characterized by the use, as catalysts, of particularly expensive and toxic metal oxides such as $OsO_4$ and $Re_2O_7$.

It has also been suggested to prepare carboxylic acids from vicinal dihydroxy compounds using various oxidizers, for example, $KMnO_4$ or peracetic acid associated with $RuCl_3$ as catalyst, these suggestions, however, meeting drawbacks of the same type as those described above for those processes starting from olefines.

Thus, one object of this invention is that of providing a new and convenient catalytic process for the preparation of monocarboxylic and dicarboxylic acids, starting from olefines or from their corresponding vicinal dihydroxy compounds, that shall be free of the drawbacks and limitations of the prior art and that uses aqueous $H_2O_2$ as a oxidizing agent.

This object, as well as still others, is achieved by the process of this invention for the preparation of a monocarboxylic or dicarboxylic acid, by oxidative scission of an olefine or the corresponding vicinal dihydroxy compound. This process is characterized in that an olefine of the formula $R_1-CH=CH-R_2$ or $R_2-CH=CH_2$ or its corresponding dihydroxy compound of formula $R_1-CHOH-CHOH-R_2$ or $R_1-CHOH-CH_2OH$ (wherein $R_1$ and $R_2$ are equal to or different from each other, and possibly substituted with groups inert under the reaction conditions, represent hydrocarbon groups such as alkyls having up to 30 carbon atoms; the cycloalkyls, possibly branched and having from 3 to 12 carbon atoms; the aryls and alkylaryls having from 6 to 12 carbon atoms; and where, moreover, $R_1$ and $R_2$ may be bound to each other in such a way as to form a cyclic alkenyl or a cyclic alkyl having up to 12 carbon atoms) are made to react, under vigorous stirring, with $H_2O_2$, at a temperature between 0° and 120° C. and under a pressure between 1 and 100 atmospheres; there are used an aqueous phase containing $H_2O_2$ and an organic phase consisting of a solvent, the olefine or its corresponding vicinal dihydroxy compound, and a catalyst; in the case of olefines, the catalyst being a composition of the formula:

$$Q_3XW_4O_{24-2n}$$

wherein:
Q represents an "onium" $(R_5R_6R_7R_8M)^+$ cation;
M is chosen from among N, P, As and Sb;
$R_5$, $R_6$, $R_7$, $R_8$, equal to or different from each other, represent hydrogen atoms or hydrocarbon groups having a total of from 20 to 70 carbon atoms;
X is either an atom of P or As;
n is an integer chosen from among 0, 1 and 2;
and, in the case of the vicinal dihydroxy compounds, the catalyst is chosen from the group consisting of the composition $Q_3XW_4O_{24-2n}$, as defined above, and a catalyst obtained by reaction of tungstic acid or an alkaline tungstate with hydrogen peroxide and an "onium" $Q^+Y^-$ salt (wherein $Y^-$ is an inorganic anion) at a pH below 2.

In the following are represented the oxidative scission reactions of the olefines and of their corresponding vicinal dihydroxy compounds:

$$R_1-CH=CH-R_2 + 4H_2O_2 \longrightarrow \tag{1}$$

-continued $$R_1-C\underset{OH}{\overset{O}{\diagup\!\!\!\!\diagdown}} + R_2-C\underset{OH}{\overset{O}{\diagup\!\!\!\!\diagdown}} + 4H_2O$$

$$R_1-CH=CH_2 + 5H_2O_2 \longrightarrow R_1-C\underset{OH}{\overset{O}{\diagup\!\!\!\!\diagdown}} + CO_2 + 6H_2O \quad (2)$$

$$R_1-CHOH-CHOH-R_2 + 3H_2O_2 \longrightarrow \quad (3)$$

$$R_1-C\underset{OH}{\overset{O}{\diagup\!\!\!\!\diagdown}} + R_2-C\underset{OH}{\overset{O}{\diagup\!\!\!\!\diagdown}} + 4H_2O$$

$$R_1-CHOH-CH_2OH + 4H_2O_2 \longrightarrow \quad (4)$$

$$R_1-C\underset{OH}{\overset{O}{\diagup\!\!\!\!\diagdown}} + CO_2 + 6H_2O$$

As can be seen from the above, reactions (1) and (3) produce two different carboxylic acids:

$$R_1-C\underset{OH}{\overset{O}{\diagup\!\!\!\!\diagdown}} \quad \text{and} \quad R_2-C\underset{OH}{\overset{O}{\diagup\!\!\!\!\diagdown}}$$

However, when $R_1$ is equal to $R_2$, only one acid is obtained.

When the olefine $R_1$—CH=CH$_2$ or the vicinal dihydroxy compound $R_1$—CHOH—CH$_2$OH are terminal, there are formed $$R_1-C\underset{OH}{\overset{O}{\diagup\!\!\!\!\diagdown}}$$

and formic acid, which may be oxidized in the reaction medium to $CO_2$; in the case of complete oxidation of $$HC\underset{OH}{\overset{O}{\diagup\!\!\!\!\diagdown}}$$

to $CO_2$, we get reactions (2) and (4).

If $R_1$ and $R_2$ are bound together in such a way as to form a ring, there is obtained a dicarboxylic acid schematically represented by the formula:

$$C\underset{OH}{\overset{O}{\diagup\!\!\!\!\diagdown}}-R_1-R_2-C\underset{OH}{\overset{O}{\diagup\!\!\!\!\diagdown}}$$

The compositions of formula $Q_3XW_4O_{24-2n}$ and their manner of preparation are described in European Patent Application No. 83/306883, filed on Nov. 10, 1983, corresponding to Italian Application No. 24154 A/82. These catalysts may be prepared in the following way:

The tungstic acid or an alkaline tungstate and the phosphoric acid or an alkaline phosphate (or a corresponding arsenic compound) are first made to react in an aqueous acid phase with $H_2O_2$, at a temperature between 20° and 80° C.; the acid aqueous phase has preferably a pH value below 2; in order to reach such a value the pH is corrected, if necessary, with a mineral acid (for example, $H_2SO_4$ or HCl). Subsequently there is added, preferably at room temperature, an "onium" salt contained in an organic solvent immiscible with water (for instance, dichloroethane or benzene). The "onium" $Q^+Y^-$ salt consists of a $Q^+$ cation, as already defined, and of an inorganic $Y^-$ anion that is stable under reaction conditions, such as, for example, $Cl^-$, $HSO_4^-$ or $NO_3^-$. The stirring of the biphasic mixture is carried on for 15–30 minutes.

The molar ratios between the reactants are usually the following: for each gram atom of X (P or As), there are used at least 4 grams atoms of W and up to 2 mols of an "onium" salt. So far as the $H_2O_2$ is concerned, from 2.5 to 6 mols of $H_2O_2$ per each gram atom of W will suffice.

If the product thus formed turns up in the solid state, it is directly separated from the biphasic mixture, for example, by filtering. In the contrary case, there will be a separated organic phase which will be filtered and evaporated under vacuum at between 40° and 50° C., thereby obtaining the catalyst in the form of a solid or of a thick oil.

Among the catalysts of formula $Q_3XW_4O_{24-2n}$, there are preferred those in which the radicals $R_5$, $R_6$, $R_7$ and $R_8$ of the "onium" Q cation have a total from 25 to 40 carbon atoms.

As far as the second type of catalyst is concerned, i.e., the one obtained by reaction of tungstic acid or of an alkaline tungstate with hydrogen peroxide and with an "onium" $Q^+Y^-$ salt (wherein $Y^-$ is an inorganic anion) at a pH below 2, this catalyst may be prepared in the following way:

Tungstic acid, or one of its alkaline salts, is suspended or dissolved in water in the presence of $H_2O_2$ at a temperature between 20° and 80° C. The pH of this solution or suspension is, if required, corrected by means of a mineral acid (for example, $H_2SO_4$ or HCl), to a pH value below 2 (and preferably a value equal to or greater than 0, but below 2).

Then, under stirring, there is admixed, preferably at room temperature, an "onium" $Q^+Y^-$ salt (wherein $Y^-$ is, for example, $Cl^-$, $HSO_4^-$ or $NO_3^-$) dissolved in an organic water immiscible solvent (for instance, benzene or dichloroethane).

The ratios between the reactants are usually the following: for 1 gram atom of W there are used from 3 to 5 mols of $H_2O_2$ and from 0.4 to 1 mol of "onium" salt. The stirring of the biphasic mixture is carried on for 15–30 minutes. At the end, the organic phase is separated, filtered and evaporated under vacuum at 40°–50° C., thereby obtaining a thick yellow oil that is the desired catalyst.

The second type of catalyst may also be prepared in situ in the reaction medium. For this purpose, into the reactor are placed the tungstic acid or an alkaline tungstate, the hydrogen peroxide, the "onium" salt, the vicinal dihydroxy compound, the solvent and, if required, a mineral acid ($H_2SO_4$ or HCl) in a quantity sufficient to bring the pH of the aqueous phase to a value below 2.

In place of the tungstic acid or of the tungstate, there may also be used tungsten compounds capable of being transformed into tungstate ion in the reaction medium. Suited for this purpose are, e.g., $WO_2$, $W_2O_5$, $WO_3$, $WS_2$, $WS_3$, $WCl_6$, $WOCl_4$ and $W(CO)_6$.

Also as far as the second type of catalyst is concerned, there are to be preferred the "onium" salts in which the radicals $R_5$, $R_6$, $R_7$ and $R_8$ of the "onium" Q cation have a total of from 25 to 40 carbon atoms.

In the preparation of carboxylic acids starting from vicinal dihydroxy compounds, the catalysts of formula $Q_3XW_4O_{24-2n}$ in general ensure better yields than those obtainable with the second type of catalysts, and are therefore the preferred ones.

As solvents for the organic phase, inert solvents are used that are substantially immiscible with the aqueous phase. For example, there may be used: (1) aromatic hydrocarbons as, for instance, benzene, toluene and the xylenes; (2) chlorinated hydrocarbons such as, for example, dichloromethane, trichloromethane, chloroethane, chloropropanes, dichloroethanes, trichloroethanes, tetrachloroethanes, dichloropropanes, trichloropropanes, tetrachloropropanes, chlorobenzene; (3) alkyl esters such as, for example, ethyl acetate. Suitable mixtures of the above solvents may also be used.

The $R_1$ and $R_2$ groups of the starting olefines and of the starting vicinal dihydroxy compounds may, if desired, carry groups (usually from 1 to 4) that are inert under the reaction conditions. These inert groups are, for instance, the hydroxyl group, chlorine, fluorine, a nitro group, an alkoxy $OR_9$ group (wherein $R_9$ is a hydrocarbon group having up to 10 carbon atoms), a ketone group, a carboxylic group, an ester $COOR_{10}$ group (wherein $R_{10}$ is a hydrocarbon group having up to 10 carbon atoms), an amide group, or a nitrile group.

Among aliphatic and cycloaliphatic unsaturated hydrocarbons oxidizable to carboxylic acids by the process of the present invention may be mentioned, for instance: 1-hexene, 1-octene, 1-decene, 1-dodecene, 1-tetradecene, 1-nonadecene, 1-eicosene, 2-hexene, 2-octene, 4-octene, cyclopentene, cyclohexene, cycloheptene, cyclooctene, cyclododecene, 1,5-hexadiene, and cuts of n-α-olefines, such as those derived from the cracking of n-paraffins as, for instance, cuts of $C_6$–$C_{10}$, $C_{10}$–$C_{15}$ and $C_{15}$–$C_{18}$ carbon atom content.

Among unsaturated aromatic hydrocarbons, there may be cited, for example: styrene, stilbenes and vinylnaphthalene.

Among olefinic compounds containing functional groups that are inert under the reaction conditions, there may be cited, for example: undecylenic acid, oleic acid, and elaidic acid.

Among vicinal dihydroxy compounds oxidizable to carboxylic acids by the process of the present invention, there may be cited the vicinal dihydroxy compounds corresponding to the above-cited unsaturated hydrocarbons, for example, 1,2-dodecanediol, 1,2-octanediol, 1,2-cyclohexanediol, 1,2-cycloheptanediol, 1-phenyl-1,2-ethanediol, 1,2-hexanediol, 4,5-octanediol, 6,7-dodecanediol, 1,2-diphenyl-1,2-ethanediol, and 1,2-cyclopentanediol.

As already indicated, the reaction between the olefine or the vicinal dihydroxy compound and the $H_2O_2$ in the presence of the catalyst occurs under vigorous stirring; by the term "vigorous stirring" is intended such a stirring as will allow a continuous mixing throughout the organic phase with the aqueous phase.

The reaction is carried out with the so-called phase-transfer technique in a biphasic aqueous liquid/organic liquid consisting of:

(a) an organic phase containing a solvent, the olefine or the vicinal dihydroxy compound, and the catalyst; and (b) an aqueous phase containing the $H_2O_2$.

The operational temperature is in practice determined by the reactivity and by the nature of the olefine or of the vicinal dihydroxy compound and by the stability of the hydrogen peroxide and of the catalyst used. Generally speaking, one operates at temperatures between 20° and 120° C. and, more commonly, at temperatures between 40° and 90° C.

Starting from olefines, the operational pressure is generally atmospheric pressure. However, in the case of low-boiling olefines, it is necessary to operate at a pressure that shall be sufficient (up to 100 atmospheres) to maintain the olefine in the liquid state.

The pressure is substantially atmospheric pressure when one starts from vicinal dihydroxy compounds.

The reactants ($H_2O_2$ and olefine or vicinal dihydroxy compound) are used substantially according to the molar ratios corresponding to the stoichiometry of the reactions from (1) to (4), as set forth above. However, it is preferred to use a moderate excess (for example, about 10%) of $H_2O_2$ with respect to the stoichiometry.

The catalyst is used in quantities generally between 0.01 and 1 gram atom of W per one mol of substrate (olefine or vicinal dihydroxy compound), but preferably between about 0.05 and about 0.15 gram atom per mol of substrate.

The concentration of the olefine or of the vicinal dihydroxy compound in the organic phase in general is between 5% and 95% by weight, but preferably between about 20% and about 50% by weight.

The concentration of the $H_2O_2$ in the aqueous phase in general is between 1% and 70% by weight, but preferably is between about 10% and about 50%.

In some cases, in order to obtain better yields, it has proved to be convenient to add to the reaction mixture small quantities of p-tert.butylphenol as inhibitor of radical reactions.

The duration of the reaction depends on the nature and on the quantity of catalyst and on the type of solvent and of olefine or vicinal dihydroxy compound used. In general, a period of time between 4 and 15 hours is sufficient for completing the reaction.

At the end of the reaction, the acid or the acids may be recovered from the reaction medium by recourse to conventional techniques for such recovery.

The organic acids obtained by the process of the present invention find a variety of applications. For example, the adipic acid is used in the production of polyamides, while the esters of azelaic and pelargonic acids are used as plasticizers.

Using starting olefines of the type

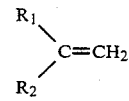

or vicinal dihydroxy compounds of the type

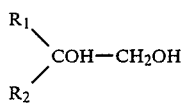

there may be formed ketones instead of acids.

The following examples are given in order to still better illustrate the inventive idea of the present invention.

EXAMPLE 1

Into a 100 ml flask, provided with a reflux condenser and a magnetic stirrer, there were loaded: 1.4 g of the composition $[(C_8H_{17})_3NCH_3]_3PW_4O_{22}$ (equal to about 2.5 mmols of W), 5 ml of 1,2-dichloroethane, 2.24 g (20 mmols) of 1-octene, 9.35 ml of $H_2O_2$ at 400 g/lt (110 mmols), and about 2 mg of p-(tert.-butyl)phenol. The resulting mixture is brought up, under vigorous stirring, to 80° C., and is then maintained at this temperature for 6.5 hours. The phases are then separated. The aqueous phase is extracted three times with 1,2-dichloroethane in order to extract the acids dissolved in water, after which the extract is added to the organic phase.

The organic phase is extracted with $Na_2CO_3$ solution in a 10% concentration (3×10 ml), after which it is eluted with n-hexane on an ion exchange resin of the sulphonic type in an acid form (Dowex 50W, 50–100 mesh) in order to free the acids from their quaternary ammonium salts, and the eluted substance containing the acids is extracted again with 10% $Na_2CO_3$ solution.

The basic aqueous extracts thus obtained are then reunited and acidified with 10% HCl. The resulting mixture is then extracted with n-hexane (3×20 ml). By evaporation of the hexane there are obtained 1.73 g of $C_6$–$C_8$ acids, of which 94.7% (measured by gas chromatography) consisted of enanthic ($C_7$) acid. The yield in enanthic acid amounted to 63% (calculated on the olefine).

EXAMPLE 2

Example 1 was repeated, but using the composition $[(C_8H_{17})_3NCH_3]_3AsW_4O_{20}$ (1.4 g; 2.5 mmols). There were obtained 1.78 g of $C_6$–$C_8$ acids, 94.6% of which consisted of enanthic acid ($C_7$). The yield in enanthic acid equalled 65%.

EXAMPLE 3

Example 1 was repeated in the absence of the p-(tert.butyl)-phenol, and using styrene (2.08 g; 20 mmols) instead of 1-octene.

After acidification of the aqueous basic extracts with HCl in a 10% concentration, the crystalline solid thus obtained was filtered, washed with $H_2O$, dried on $P_2O_5$, and then dissolved in ether.

By evaporation of the preliminarily filtered etheric solution, there were obtained 1.83 g of benzoic acid with a 97.7% titer, and with a yield of 73%.

EXAMPLE 4

Example 1 was repeated, but using oleic acid (5.65 g; 20 mmols) instead of 1-octene, 7.50 ml instead of 9.35 ml of $H_2O_2$ at 400 g/lt (88.2 mmols), and by reducing the reaction time down to 5 hours. Then, the reaction mixture was allowed to rest overnight in a refrigerator (0°–5° C.).

After filtering of the solid that had formed and after successive separation of the phases, the procedure was as in Example 1.

The solid, gathered by filtering, was added to the residual oil obtained by evaporation of the n-hexane, and the resulting mixture was eluted on a silicon column (70–230 mesh; eluent; acetone/n-hexane 1:1), gathering the fractions having $R_f$=0.5–0.9.

In this way there were obtained 5.48 g of product consisting of 56.7% of azelaic acid (yield: 83%), 37.9% of pelargonic acid (yield: 66%), and 1.8% of caprylic ($C_8$) acid.

EXAMPLE 5

Example 1 was repeated, but using 1-dodecene (3.36 g; 20 mmols) instead of 1-octene.

The residual oil, obtained by evaporation of the n-hexane, was eluted in a silicon column (70–230 mesh; eluent: ether/n-hexane 1:1), gathering the fractions having $R_f$ of about 0.5–0.6.

By evaporation of the solvent there were obtained in this way 2.04 g of $C_8$–$C_{11}$ acids, of which 90.1% was undecanoic acid ($C_{11}$). The yield in undecanoic acid amounted to 49%.

EXAMPLE 6

Into a 100 ml flask, provided with a reflux condenser and a magnetic stirrer, were loaded 1.4 g (equal to about 2.5 mmols of W) of the catalytic composition of Example 1, 10 ml of 1,2-dichloroethane, 4.26 g (52 mmols) of cyclohexene, and 19.55 ml of $H_2O_2$ at a concentration of 400 g/lt (230 mmols).

This mixture was brought up, under vigorous stirring, to 70° C. and was then maintained at that temperature for 16 hours. Then, the mixture was allowed to rest overnight in a refrigerator (at 0°–5° C.).

After filtering, the crystals that had thus formed, and after separation of the phases, into the aqueous phase, there were first bubbled through $SO_2$ until complete destruction of the residual $H_2O_2$, and the $N_2$, in order to remove the excess $SO_2$.

The aqueous solution was thereupon rendered basic with NaOH in a 10% concentration to a pH of about 8 and was then brought to dryness at 60° C. under vacuum.

The residue was extracted for 40 minutes with acetone at boiling temperature. The mixture was then filtered and the solid thus obtained was dissolved in water and concentrated to the minimum volume possible. The solution was then acidified with a few drops of concentrated HCl and was then allowed to crystallize in a refrigerator.

The crystals thus obtained, added to those gathered previously, were washed with 1,2-dichloroethane, then with icy water (2 ml) and then, first dried at the water pump and then in an oven for 2 hours at 80° C.

There was thus obtained 5.43 g of a 99% adipic acid, which corresponded to a yield of 71%.

EXAMPLE 7

Example 1 was repeated, but using trans-2-octene (2.24 g; 20 mmols) instead of 1-octene.

Both the organic phase at the end of the test as well as the end extract in n-hexane, containing the desired product, were repeatedly shaken with water in order to remove possible traces of residual acetic acid.

In this way there were obtained 1.88 g of $C_5$–$C_8$ acids, which consisted of 96.3% of capronic ($C_6$) acid. The yield in capronic acid amounted to 78%.

EXAMPLE 8

Example 4 was repeated, using 1,2-octanediol (2.92 g; 20 mmols), but using 20 mmols of 1,2-dichloroethane and prolonging the reaction time to 7 hours.

At the end of the reaction, the procedure was as in Example 1. There were thus obtained 2 g of $C_6$–$C_8$ acids, of which 96.5% consisted of enanthic ($C_7$) acid. The yield in enanthic acid amounted to 74%.

EXAMPLE 9

Into a 250 ml flask, fitted with a reflux condenser and a magnetic stirrer, there were loaded 1.4 g (equal to about 2.5 mmols of W) of the composition of Example 1, 80 ml of 1,2-dichloroethane, 6 g (51.7 mmols) of 1,2-cyclohexanediol (cis+trans mixture), and 14.45 ml of $H_2O_2$ in a 400 g/lt concentration (170 mmols).

The mixture was thereupon brought up, under vigorous stirring, to 70° C. and was then maintained at this temperature for 14 hours. At the end of this period, the procedure was as in Example 6. There were obtained 6.15 g of a 95.6% adipic acid, which corresponded to a yield of 78%.

EXAMPLE 10

Into a 100 ml flask, fitted with a reflux condenser and a magnetic stirrer, there were introduced 1.65 grams of $Na_2WO_4.2H_2O$ (5 mmols), 15 ml of $H_2O$, 1.5 ml of $H_2O_2$ at a 400 g/liter concentration (17.6 mmols), and then there was admixed $H_2SO_4$ in a 30% concentration until a pH of about 1 was reached.

To this solution, kept under stirring, there were then added dropwise in about 2 minutes, 0.8 g (about 2 mmols) of trioctylmethylammonium chloride dissolved in 20 ml of 1,2-dichloroethane. After 15 minutes of further stirring, the organic phase was separated and filtered, and then used as indicated in the following.

To the above-said solution of 1,2-dichloroethane, containing the catalyst (about 2 mmols of W), there were added 2.92 g (20 mmols) of 1,2-octanediol, 7.65 ml of $H_2O_2$ in a 400 g/lt concentration (90 mmols), and about 2 mg of p-(tert.butyl)phenol.

This mixture was then brought, under vigorous stirring, up to 80° C. and was then maintained at this temperature for 7 hours. The procedure then was as in Example 1, thereby obtaining 1.78 g of $C_6$–$C_8$ acids, of which 96.7% consisted of enanthic ($C_7$) acid. The yield in enanthic acid amounted to 66%.

EXAMPLE 11

Example 1 was repeated, using 46.75 ml of $H_2O_2$ in an 80 g/liter concentration (100 mmols).

There were obtained 1.95 g of $C_6$–$C_8$ acids, of which 90.2% consisted of enanthic ($C_7$) acid. The yield in enanthic acid amounted to 68%.

What is claimed is:

1. A process for preparing a monocarboxylic or dicarboxylic acid by oxidative scission of an olefine or a vicinal dihydroxy compound, characterized in that an olefine of the formula $R_1$—CH=CH—$R_2$ or $R_1$—CH=$CH_2$ or a vicinal dihydroxy compound of formula $R_1$—CHOH—CHOH—$R_2$ or $R_1$—CHOH—$CH_2$—OH (wherein $R_1$ and $R_2$, either equal to or different from each other and, optionally, substituted with groups inert under the reaction conditions, represent hydrocarbon groups such as alkyls having up to 30 carbon atoms; cycloalkyls, optionally branched, having from 3 to 12 carbon atoms; aryls and alkylaryls having from 6 to 12 carbon atoms; moreover, $R_1$ and $R_2$ may be bound to each other therefore forming a cyclic alkenyl or cyclic alkyl having up to 12 carbon atoms) are reacted, under vigorous stirring, with $H_2O_2$ at a temperature between 0° and 120° C. and under a pressure between 1 and 100 atmospheres; and there are used an aqueous phase containing $H_2O_2$ and an organic phase consisting of a solvent, the olefine or the vicinal dihydroxy compound, and a catalyst; in the case of the olefines, the catalyst being a composition of the formula:

$$Q_3XW_4O_{24-2n}$$

wherein:

Q represents an "onium" $(R_5R_6R_7R_8M)^+$ cation in which M is chosen from the group of N, P, As and Sb;

$R_5$, $R_6$, $R_7$, $R_8$, equal to or different from each other, represent hydrogen atoms or hydrocarbon groups having a total of from 20 to 70 carbon atoms;

X is an atom of P or As;

n is an integer chosen from among 0, 1 and 2;

and, in the case of the vicinal dihydroxy compounds, the catalyst is chosen from the group consisting of the composition $Q_3XW_4O_{24-2n}$, as defined above, and a catalyst obtained by the reaction of tungstic acid or an alkaline tungstate, with hydrogen peroxide and an "onium" $Q^+Y^-$ salt (wherein $Y^-$ is an inorganic anion) at a pH below 2.

2. A process according to claim 1, characterized in that in the catalyst, the radicals $R_5$, $R_6$, $R_7$ and $R_8$ of the "onium" $(R_5R_6R_7R_8M)^+$ cation have a total of from 25 to 40 carbon atoms.

3. A process according to claim 1 or 2, characterized in that the catalyst obtained by the reaction of tungstic acid or of an alkaline tungstate with hydrogen peroxide and an onium salt, is prepared in situ in the reaction medium, introducing into said medium tungstic acid or an alkaline tungstate, hydrogen peroxide, the onium salt, the vicinal dihydroxy compound, the solvent and, optionally, a mineral acid in a quantity sufficient to bring the pH to a value below 2.

4. A process according to claim 3, characterized in that instead of introducing into the reaction medium tungstic acid or an alkaline tungstate, there are introduced tungsten compounds capable of being transformed into tungstate ions in the reaction medium, such as $WO_2$, $W_2O_5$, $WO_3$, $WS_2$, $WS_3$, $WCl_6$, $WOCl_4$ and $W(CO)_6$.

5. A process according to claim 1, characterized in that the solvent is an aromatic hydrocarbon, a chlorinated hydrocarbon, or an alkyl ester.

6. A process according to claim 1, characterized in that the reaction temperature is between 40° and 90° C.

7. A process according to claim 1, characterized in that when one starts from a vicinal dihydroxy compound, the pressure is substantially atmospheric pressure.

8. A process according to claim 1, characterized in that the catalyst is used in a quantity between 0.01 and 1 gram atom of W per mol of olefine or of vicinal dihydroxy compound.

* * * * *